(12) United States Patent
Birdsall et al.

(10) Patent No.: US 7,208,172 B2
(45) Date of Patent: Apr. 24, 2007

(54) METALLIC COMPOSITE COATING FOR DELIVERY OF THERAPEUTIC AGENTS FROM THE SURFACE OF IMPLANTABLE DEVICES

(75) Inventors: Matthew J. Birdsall, Santa Rosa, CA (US); Richard L. Klein, Santa Rosa, CA (US); Nathan Maier, Forestville, CA (US)

(73) Assignee: Medlogics Device Corporation, Santa Rosa, CA (US)

( * ) Notice: Subject to any disclaimer, the term of this patent is extended or adjusted under 35 U.S.C. 154(b) by 191 days.

(21) Appl. No.: 10/701,262

(22) Filed: Nov. 3, 2003

(65) Prior Publication Data

US 2005/0092615 A1 May 5, 2005

(51) Int. Cl.
*A61F 2/02* (2006.01)
(52) U.S. Cl. ....................................... 424/423
(58) Field of Classification Search ................. 424/423
See application file for complete search history.

(56) References Cited

U.S. PATENT DOCUMENTS

| | | | |
|---|---|---|---|
| 3,936,577 A | 2/1976 | Christini et al. |
| 4,358,922 A | 11/1982 | Feldstein |
| 4,374,669 A | 2/1983 | Mac Gregor |
| 4,397,812 A | 8/1983 | Mallory, Jr. |
| 4,547,407 A | 10/1985 | Spencer, Jr. |
| 4,729,871 A | 3/1988 | Morimoto |
| 4,917,895 A | 4/1990 | Lee et al. |
| 5,064,435 A | 11/1991 | Porter |
| 5,145,517 A | 9/1992 | Felstein et al. |
| 5,464,650 A | 11/1995 | Berg et al. |
| 5,545,208 A | 8/1996 | Wolff et al. |
| 5,725,570 A | 3/1998 | Heath |
| 5,725,572 A | 3/1998 | Lam et al. |
| 5,772,864 A | 6/1998 | Moller et al. |
| 5,837,313 A | 11/1998 | Ding et al. |
| 5,843,172 A | 12/1998 | Yan |
| 5,873,904 A | 2/1999 | Ragheb et al. |
| 5,958,430 A | 9/1999 | Campbell et al. |
| 5,972,027 A | 10/1999 | Johnson |
| 5,976,169 A | 11/1999 | Imran |
| 6,019,784 A | 2/2000 | Hines |
| 6,120,536 A | 9/2000 | Ding et al. |
| 6,123,861 A | 9/2000 | Santini, Jr. et al. |
| 6,174,329 B1 | 1/2001 | Callol et al. |
| 6,180,162 B1 | 1/2001 | Shigeru et al. |
| 6,240,616 B1 | 6/2001 | Yan |
| 6,253,443 B1 | 7/2001 | Johnson |
| 6,273,913 B1 | 8/2001 | Wright et al. |
| 6,287,249 B1 | 9/2001 | Tam et al. |
| 6,287,285 B1 | 9/2001 | Michal et al. |
| 6,287,331 B1 | 9/2001 | Heath |
| 6,290,721 B1 | 9/2001 | Heath |
| 6,299,604 B1 | 10/2001 | Ragheb et al. |
| 6,315,794 B1 | 11/2001 | Richter |
| 6,355,058 B1 | 3/2002 | Pacetti et al. |
| 6,447,664 B1 | 9/2002 | Taskovics et al. |
| 6,475,644 B1 | 11/2002 | Hampikian et al. |
| 6,599,928 B2 | 7/2003 | Kunz et al. |
| 6,716,444 B1 | 4/2004 | Castro et al. |
| 6,730,064 B2 | 5/2004 | Ragheb et al. |
| 2002/0055770 A1 | 5/2002 | Doran et al. |
| 2003/0028242 A1 | 2/2003 | Vallana et al. |
| 2003/0096064 A1 | 5/2003 | Suda et al. |

FOREIGN PATENT DOCUMENTS

| | | |
|---|---|---|
| EP | 0470 246 B1 | 6/1995 |
| EP | 0 850 604 B1 | 7/1998 |
| EP | 0 916 317 A1 | 5/1999 |
| EP | 0 633 798 B1 | 5/2003 |
| GB | 1137960 | 12/1968 |
| WO | WO 93/19803 | 10/1993 |
| WO | WO 99/25272 | 5/1999 |
| WO | WO 00/29501 | 5/2000 |
| WO | WO 01/14617 A1 | 3/2001 |
| WO | WO 01/15751 A1 | 3/2001 |
| WO | WO 01/70294 A2 | 9/2001 |
| WO | WO 02/058775 A2 | 8/2002 |
| WO | WO 02/078785 A2 | 10/2002 |

(Continued)

OTHER PUBLICATIONS

Kaisheva, et al.; "Influence of the Surface Properties of SIC Particles on Their Codeposition with Nickel," *Journal of The Electrochemical Society*; 2004; pp. C89-C96; vol. 151; No. 1; The Electrochemical Society.

(Continued)

*Primary Examiner*—Carlos A. Azpuru
(74) *Attorney, Agent, or Firm*—C. Rachal Winger; Kirkpatrick & Lockhart Preston Gates Ellis LLP

(57) ABSTRACT

A metallic composite coating, and methods for forming same, for an implantable medical device is disclosed. The composite coating comprises at least one metal or metallic tie layer formed on the surface of the device, followed by an electroless electrochemical cladding of one or more additional layers over the tie layer. One or more therapeutic or biologically active agents are co-deposited with at least one of the electroless electrochemical claddings.

10 Claims, No Drawings

FOREIGN PATENT DOCUMENTS

WO       WO 03/045582 A1     6/2003
WO      WO 2004/0432992 A2    5/2004

OTHER PUBLICATIONS

Jeanmenne, Robert A. Jr., et al.; "Electroless Plating on Medical Catheters," PF Online Feature Article; pp. 1-4.

Gertner, M.E. & M. Schlesinger; "Electrochemistry and Medical Devices Friend or Foe?," *The Electrochemical Society Interface*, Fall 2003; pp. 20-24.

Schlesinger, Mordechay & Milan Paunovic; "Electroless Deposition of Nickel,"; *Modern Electroplating*, 2000, pp. 667-737, 4th Edition, John Wiley & Sons, Inc., Canada.

Gertner, Michael E. & M. Schlesinger, "Drug Delivery From Electrochemically Deposited Thin Metal Films," Electrochemical and Solid-State Letters, Feb. 7, 2003, 6(4): pp. J4-J6.

Fields, William D. et al.; "Electroless Nickel Plating," New Market Development, Allied-Kelite. Division of the Richardson Co., pp. 219-242.

Hajdu, Juan; "Chapter 7—Surface Preparation for Electroless Nickel Plating," pp. 193-206.

METALLIC COMPOSITE COATING FOR DELIVERY OF THERAPEUTIC AGENTS FROM THE SURFACE OF IMPLANTABLE DEVICES

BACKGROUND OF THE INVENTION

This present invention relates generally to depositing a thin metal coating onto the surface of implantable devices to achieve a more desirable device-tissue interface. More specifically, to a passive or non-reactive metallic coating incorporating one or more bioactive materials on the surface of an implantable device. And, more particularly, to electrochemically depositing a metallic coating incorporating one or more therapeutic agents onto a deformable structure for maintaining the patency of stenotic, occluded or diseased lumens post-implantation of the structure.

Implantable devices include, for example, stents, stent-grafts, embolic filters, detachable coils, pacemaker and defibrillator leads, plates, screws, spinal cages, dental implants, ventricular assist devices, artificial hearts, artificial heart valves, annuloplasty devices, artificial joints, and implantable sensors. Frequently, implanted medical apparatus must be designed to be sufficiently biocompatible to the host body. Otherwise, the body will manifest a rejection of the implant by way of a thrombotic, inflammatory or other deleterious response.

Such implantable devices, therefore, are designed or fabricated from materials possessing surface properties that minimize bodily response at the tissue-device interface. For example, stainless steel is a frequently used implant material due to the relatively passive oxide layer which forms on its surface. Moreover, much activity recently has been directed towards local delivery of bioactive materials into the target tissue via the device being implanted therein. Such bioactive materials are not limited to therapies for treating diseased or abnormal conditions, but also for minimizing the body's response to both the presence of and injury caused to the tissue during the implantation procedure.

These bioactive materials can include, without limitation, anti-inflammatory agents, anti-infective agents, anti-cancer agents, as well as agents used for vascular disease such as anti-restenosis compounds and anti-coagulant compounds. With regard to the latter, much research and development has been devoted to one particular implantable medical device for local delivery of bioactive compounds for treating vascular disease, more specifically, stents.

In recent years, intervention in the form of stenting has become widespread in the treatment of peripheral and coronary vascular disease. Stents are mechanical scaffolding devices typically used to maintain the patency of the previously occluded or stenosed vessel following or during percutaneous translumenal angioplasty (PTA) or percutaneous translumenal coronary angioplasty (PTCA). PTA or PTCA typically involves advancing a catheter, having an inflatable balloon on the distal end thereof, through a patient's arterial system until the balloon crosses an atherosclerotic lesion. The balloon is then inflated to dilate the artery. After dilation, the balloon is deflated and the catheter removed leaving an enlarged arterial passageway or lumen, thereby increasing blood flow. Following this procedure, a stent delivery system, which, in the instance of a balloon-expandable stent consists of a stent mounted on a similar balloon catheter or in the instance of a self-expanding stent consists of a stent loaded into the distal end of a delivery catheter, is advanced to the site, expanded and left in-situ to scaffold or prop-up the artery and maintain its patency. Alternatively, in certain procedures, the first step of pre-dilatation may be omitted in favor a direct stenting procedure whereby the stent delivery system dilates at the time of stenting. A significant number of PTA and PTCA procedures, however, result in a restenosis or re-narrowing of the lumen.

Re-narrowing or restenosis of the treated arteries, for example, occurs at a rate of 20% to 50% in patients undergoing this procedure, requiring repeat intervention either, for example, by further stenting, vascular grafting, debulking or bypass surgery. Any one individual's restenosis rate is dependent upon a number of morphological and clinical variables.

In addition to, and with respect to coronary artery intervention, the cellular response from angioplasty or stenting which, besides opening a previously occluded artery, also can cause fissuring of the atherosclerotc plaque and injury to resident arterial smooth muscle cells. In response to this injury, among other responses, hyperplasia, rapid proliferation, of smooth muscle cells occurs. Over a period of time, typically one to six months, this hyperplastic response can cause significant re-narrowing of the lumenal space opened by the intervention. For purposes of the instant invention, however, the lumen to be treated is not limited to coronary arteries, but also includes any other similar body conduit that tends to improperly constrict as a result of disease or malfunction, such as: arteries located within the mesentery, peripheral, or cerebral vasculature; veins; gastrointestinal tract; biliary tract; urethra; trachea; hepatic shunts; and fallopian tubes.

There are two general categories of stents, self-expanding stents and balloon-expandable stents. Self-expanding stents are typically made from nickel-titanium alloys, such as NITINOL, or stainless steel wire or wire braid. Such stents are typically compressed into a first shape and inserted into a sheath or cartridge positioned at the distal end of a delivery device. When the stent is positioned across the lesion, the sheath is withdrawn causing the stent to radially expand and abut the vessel wall. Balloon-expandable stents are typically introduced into a lumen on a catheter having an inflatable balloon on the distal end thereof. When the stent is at the desired location in the lumen, the balloon is inflated to circumferentially expand the stent. The balloon is then deflated and the catheter is withdrawn, leaving the circumferentially expanded stent in the lumen, usually as a permanent prosthesis for helping to hold the lumen open.

Attempts, both mechanical and pharmacological, to address restenosis include providing a suitable surface within the lumen for more controlled healing to occur in addition to the support provided by a stent. Mechanical attempts include providing a lining or covering in conjunction with a stent, a stent-graft. The covering of a stent-graft may prevent excessive tissue prolapse or protrusion of tissue growth through the interstices of the stent while allowing limited tissue in-growth to occur to enhance the implantation. The surface of the graft material at the same time prevents scarring from occluding the lumen and minimizes the contact between the fissured plaque and the hematological elements in the bloodstream. Both self-expanding and balloon-expandable stents can be used in conjunction with a covering or lining.

Pharmacological attempts have involved systemic delivery of drugs either orally, intravascularly or intramuscularly. And, more recently, drug eluting stents. These drug eluting stents typically involve a balloon-expandable stent modified to deliver anti-thrombotic or anti-restenotic compounds. Such devices typically involve the application of a coating, specifically adapted to hold and release drugs, to the surface of the stent. Many such coatings are polymers that perform such a hold and release function. These polymers can be degradeable, wherein the coating releases the drug via degradation of the polymer, or non-degradeable, whereby the drug diffuses therefrom into the surrounding environment.

These polymeric coatings, however, have certain limitations and shortcomings. In one regard, the degradation kinetics of polymers is often unpredictable. Consequently, it is difficult to predict how quickly a bioactive agent in a polymeric medium will be released. If a drug releases too quickly or too slowly from the polymeric medium, the intended therapeutic effect may not be achieved. In another aspect, in some instances, polymeric materials produce an inflammatory response. For example, certain polymeric coatings on stents have been observed to produce an inflammatory response, exascerbating restenosis. Moreover, yet another difficulty with polymers is their adherance to a substantially different substrate, such as a metal substrate, is difficult to achieve in manufacturing and to maintain after implantation. Mismatched properties such as different thermal and/or mechanical properties between the polymeric coating and the underlying substrate contribute to this difficulty.

Inadequate bonding or adhesion between a stent and an overlying polymeric coating may result in separation of these components over time, an undesirable characteristic for an implanted medical device to exhibit. Such separation is even more susceptible at areas of the stent subject to greater amounts of deflection during expansion, such as the apices or crowns of the stent.

Yet another limitation, is that it is difficult to evenly coat complex geometries and small objects not to mention small, complex metallic objects with a polymeric material. Therefore, small metallic objects, such as stents, become more difficult to coat evenly with a polymeric material. Yet a further limitation of polymer coatings is that they contribute bulk but do not contribute to the function of a stent which is to maintain lumen patency.

One proposed alternative to polymer coating is sintering. In such a sintering process, a heat and/or pressure treatment is used to weld small particles of metal to the surface of the structure. A porous metallic structure is created. Such sintered metallic structures, however, exhibit relatively large pores. When a bioactive material is loaded into the pores of a sintered metallic structure, the larger pore size can cause the biologically active material to release too quickly, possibly during delivery to the intended tissue. Also, because a high temperature is used to form a sintered structure, a bioactive material must be loaded into the sintered structure after the porous structure is formed. This method is not only time consuming, it is also difficult to impregnate the pores of the sintered structure with the biologically active material. Consequently, it is difficult to fully load the sintered structure with the bioactive material.

More recently, drug delivery from electrochemically deposited thin metal films has been posited. This coating process employs, as one of its steps, an electroless metal deposition. The drug to be delivered is dissolved or dispersed into a metalizing deposition bath, and is co-deposited on the implantable device. This deposition process involves the use of some heavy metals, such as stannous and palladium, to sensitize and activate the surface, which, albeit in small amounts, remains on the implantable device.

BRIEF SUMMARY OF THE INVENTION

The present invention provides a thin metal coating and coating process for coating implantable medical devices. In addition, the invention provides a relatively passive, or relatively non-reactive, external surface coating on implantable medical devices lessening the reaction to the device and improving the device-tissue interface.

One aspect of the invention is to improve adherence of the coating to the surface of the underlying implantable device.

It is also an object of the invention to incorporate one or more therapeutic agents into the coating.

In another aspect of the invention the implantable medical device is coated without signficantly increasing its bulk.

Where the implantable device is fabricated from a metal or metal alloy, another object of the invention is to provide a coating which possesses properties more compatible with the underlying substrate.

It is a further aspect of the invention to provide an improved coating on the surface of an implantable endolumenal prosthesis for maintaining lumen patency.

As previously described, certain implantable medical devices, such as stents, are limited in their material choices due to the desire to have a passive surface. For example, it is a reason why balloon-expandable stents have been fabricated from stainless steel, and, more recently, cobalt-chromium. Therefore, an additional object of the invention is to alleviate this material limitation by having a relatively passive coating encasing the stent.

It is even a further object of the invention to provide an improved thin metal coating process for deposition onto implantable endolumenal devices. Another aspect of this object is to also co-deposit therapeutic agents with and within the coating for subsequent elution from the implantable medical device.

The invention comprises forming multiple layers on the surface of a device to form a composite matrix. In a particular embodiment, a first layer is applied or struck on the surface by contacting the surface with an electrolytic solution containing metal ions, and subsequently electrodepositing a thin metal film onto the surface. This is followed by contacting the surface with a second electrochemical bath containing metal ions and one or more therapeutic agents to form a second layer on the surface of the device. The agents are co-deposited with the metal ions on the surface of the device to form a composite, bioactive, metallic matrix on the device.

In a further embodiment of the invention, the first layer is electroplated onto the surface of the device and the second layer is deposited through an electroless electrochemical co-deposition process. The invention further contemplates the application of more or more electroplated layers, and one or more layers deposited through an electroless electrochemical process. In another embodiment of the invention, the electroless electrochemical deposition steps are performed with out any pre-sensitizing of the surface nor any pre-deposition of a catalyst on the surface to be coated.

DETAILED DESCRIPTION OF THE INVENTION

The present invention relates to a thin metal coating and a process depositing the thin metal coating on implantable endolumenal medical devices. The following description is presented to enable one of ordinary skill in the art to make and use the invention and is provided in the context of a patent application and its requirements. Various modifications to the preferred embodiment will be readily apparent to those skilled in the art and the generic principles herein may be applied to other embodiments. Thus, the present invention is not intended to be limited to the embodiment shown but is to be accorded the widest scope consistent with the principles and features described herein.

This invention introduces an improved method for depositing a thin metal matrix onto the surface of an implantable device. The multiple step process deposits a composite thin metal matrix onto the device's surface. This multiple step process also includes one or more steps where a therapeutic or biologically active agent, or agents, is co-deposited with and within one or more thin metal films. The process is quite controllable and variable based on such parameters as temperature, pH, relative concentration of solution constituents, other additives or agents present in solution and time.

Specifically, the present invention makes use of the process of electroless electrochemical deposition to apply one or more layers of thin metal film, incorporating one or more biologically active agents, onto the surface of an implantable device. Electroless electrochemical deposition is a self-assembling or autocatalytic process.

More specifically, in a further embodiment, the invention combines the processes of electroplating and electroless electrochemical deposition, in a multi-step approach, to provide better adherence of the metallic matrix to the surface of the underlying device while also incorporating one or more biologically active agents with and within the coating matrix.

By one aspect of the invention, two solutions are prepared. The first being an electroplating or electrolytic solution or bath, and the second being an electroless deposition solution or bath. The first bath is formed with a cathode (the device to be coated), and an electrolytic solution containing metal ions. The second bath is formed using metal salts, a solvent, a reducing agent, and more or more biologically active agents to be incorporated into the coating matrix.

Prior to subjecting the device to the electrochemical processes described, the surface of the device must be appropriately prepared. This is done by contacting or immersing the device in a pre-treatment bath. This bath can include organic or inorganic acids. For example, with regard to alloys such as stainless steel, nickel-titanium, or cobalt-chromium an acid bath including an one or combination of inorganic acids such as hydrochloric acid (HCl), nitric acid (HNO$_3$, or hydroflouric acid (HF). Other methods of cleaning the surface can include molten salts, mechanical removal, alkaline cleaning, or any other suitable method that provides a clean, coatable surface. This initial step serves to clean the surface and etch the surface thereby removing any resident oxide layers on the structure and pitting the surface to improve subsequent adherence of the coating to the device.

The device is then rinsed, preferably deionized water and more preferably, deionized and distilled water. Although, any suitable suitable liquid or gas could be used to remove any possible impurities from the surface. After rinsing, the implantable structure to be coated is immersed in the first bath. A current is then applied across the device causing the metal ions to move to the device and plate the surface. This electroplating step causes an intermediate or "strike" layer to be formed on the surface of the device. Metal ions for this first bath are chosen to be compatible with the material making up the device itself. For example, if the underlying structure is made of cobalt chrome, cobalt ions are preferred. It has been found that this strike layer improves overall adherence of the coating to the implantable device as well as increasing the rate of deposition or efficiency of the second, electroless film. The device is subsequently removed from the first bath and rinsed again with water prior to immersion into the second bath.

The device is then immersed in the second, electroless bath at a controlled temperature and pH value. In this step, metal ions, the reducing agent, and the one or more therapeutic agents are simultaneously and substantially uniformly, co-deposited on the struck surface of the device. After immersion in this second bath, a bioactive composite metallic matrix has been formed on the surface of the device. The device is removed from the second bath and allowed to dry.

By this deposition process, any suitable structure can be coated. The device can be porous or solid, flexible or rigid, have a planar or non-planar surface. Accordingly, in some embodiments the device could be stent, a pellet, a pill, a seed, an electrode, a coil, etc. The device to be coated may be formed of any suitable material such as, metal, metal alloy, ceramic, polymer, glass, etc.

Any suitable source of metal ions can be used for the first electrolytic bath. Typically, such metal ions are derived from metal salts which dissociate from one another in solution. Such salts, and therefore ions, are well known in the field of electrolytic deposition and can be chosen by those of ordinary skill in this art. Examples of suitable metal ions depends on the underlying device to be coated, but does include ions of nickel, copper, gold, cobalt, silver, palladium, platinum, etc., and alloys thereof. Different types of salts can be used if it is desired to strike a metal alloy matrix on the surface of the device.

Similarly, any suitable source of metal ions can be used for the second electroless electrochemical deposition bath. And are also typically derived from metal salts. Examples of such suitable sources depends on the underlying device to be coated and are well known in the field of electroless electrochemical deposition and can be selected by those of ordinary skill in this art.

The electroless electrochemical solution also includes a reducing agent and may include complexing agents, buffers and stabilizers. The reducing agent reduces the oxidation state of the metal ions in solution such that the metal ions deposit on the surface of the device as metal. Complexing agents are used to hold the metal in solution. Buffers and stabilizers are used to increase bath life and improve stability of the bath. Buffers are also used to control the pH of the solution. Stabilizers are also used to keep the solution homogeneous. Examples of such complexing agents, buffers and stabilizers are well known in the field of electroless electrochemical deposition and can be selected by those of ordinary skill in this art.

Concerning the therapeutic agents to be co-deposited, any such agent, agents, or combinations thereof can be deposited within the coating depending on the condition to be treated, response desired, or tissue into which the device is to be introduced. Agents which can be coated onto the surface of the device in accordance with the invention include the following compounds; organic, inorganic, water soluble, water insoluble, hydrophobic, hydrophilic, lipophilic, large molecules, small molecules, proteins, anti-proliferatives, anti-inflammatory, anti-thrombogenetic, anti-biotic, anti-viral, hormones, growth factors, immunosuppressants, chemotherapeutic, etc.

These therapeutic agents which are co-deposited or captured within the electroless electrochemically deposited layer, diffuse out or are released from the coating via pores formed in the coating by the coating process itself. The metal composite matrix forms pores between self-assembling grains as they meet and grow on the surface being coated. This porosity, or the extent and nature of these pores, is a property that is readily manipulated according to proven methods well known to those of ordinary skill in this art.

With regard to the first electroplating bath, in another embodiment of the invention, one or more intermediate layers can be struck on the surface of the device. This can improve the efficiency of the subsequent electroless electrochemical coating step.

Likewise, with regard to the second electroless electrochemical bath, one or more films can be coated onto the surface of the device. Furthermore, multiple electroless electrochemical baths can be used such that not all these baths co-deposit one or more therapeutic agents. For example, after the electroplating step, a first electroless electrochemical bath without any therapeutic agents can be employed to place a first electroless coating onto the surface of the device. The device can then be transferred to a second electroless bath containing one or more therapeutic agents in solution. This can improve the efficiency of the step involving co-deposition of the metal ions, reducing agent and one or more therapeutic agents.

Moreover, multiple electroless baths can be prepared containing and co-depositing different biologically active agents in each coating layer. In addition, an electroless bath, not containing any therapeutic agents, can be applied as a top coat to modify or control the release of therapeutic agents from an inner layer or layers.

The invention will now be described in additional detail by way of working examples of the metallic bioactive matrix deposited on stents. The scope of the present invention, however, is not at all limited by these working examples. Nor is the implantable device limited to a stent. Rather, these examples are illustrative of a manner in which the invention can be practiced.

EXAMPLE 1

Bioactive composite coatings were formed on the surface of 7 stainless steel stents. Each stent had two tie layers of nickel struck on its surface prior to immersion in a nickel-phosphorous (Ni—P) electroless deposition bath. Rapamycin, paclitaxel, des-aspartate angiotensin I (DM-1), and a sialokinin (designated HP-1) were dissolved/suspended in the various Ni—P baths and co-deposited on the tie layer.

More specifically, each stent was first prepared by immersion in a 37% hydrochloric (HCl) acid bath at room temperature for seven minutes. The stent was then rinsed with deionized and distilled water. After rinsing, the stent was immersed in an electrolytic bath containing nickel ions, which bath was concocted by dissolving nickel chloride (NiCl) in HCl and water. The nickel strike was conducted at room temperature. A negative electric charge was then applied to the stent causing the nickel ions to aggregate on the stent surface. A charge of approximately 0.7 volts was applied for four minutes. Subsequent to this electroplating step, the stent was again rinsed in distilled, deionized water. The stents were again immersed in HCl for seven minutes and again immersed in the strike bath, with charge applied as before, for four minutes. Following this double strike, the stents were immersed into a electroless Ni—P bath for ten minutes, which bath was concocted by mixing $NiSO_4$, $NaH_2PO_2$, $Na_3C_6H_5O_7$, and $NH_4Cl$ to form a homogenous, aqueous solution. Rapamycin (sirolimus), paclitaxel, DAA-1, and HP-1 were also added to various electroless Ni—P baths, of the same composition as the above described bath, and co-deposited therewith on the surface of the stent over the tie layers and initial Ni—P layer. The electroless Ni—P and drug co-depositions were conducted at a temperature range of 37–45 C and a pH of 9.5–10 for a total of 120 minutes. Paclitaxel, DM-1 and HP-1 were added to their respective Ni—P baths at a concentration of 1.25 mg per 25 ml Ni—P solution. Rapamycin was added to its Ni—P bath at a concentration of 1 mg per 25 ml of Ni—P solution.

EXAMPLE 2

Bioactive composite coatings were formed on the surface of 6 Nitinol self-expanding stents. Each stent had a tie layer of nickel struck on its surface prior to immersion in a Ni—P electroless deposition bath. Rapamycin, DAA-1 and HP-1 were dissolved/suspended in the various Ni—P baths and co-deposited on the tie layer.

More specifically, each stent was first prepared by immersion in a bath of 2% hydroflouric (HF) and 21% nitric ($HNO_3$) acid bath at room temperature for 2 minutes. The stents were then rinsed with deionized and distilled water, and immersed in a 37% HCl acid bath at room temperature for 7 minutes. Each stent was then rinsed with deionized and distilled water. After rinsing, each stent was immersed in an electrolytic bath containing nickel ions, which bath was concocted by dissolving NiCl in HCl and water. The nickel strike was conducted at room temperature. A negative electric charge was then applied to the stent causing the nickel ions to aggregate on the stent surface. A charge of approximately 0.7 volts and 0.09 amps was applied for 4 minutes. Subsequent to this electroplating step, the stents were again rinsed in distilled, deionized water. Following the electrolytic strike, the stents were immersed into an electroless Ni—P bath for ten minutes, which bath was concocted by mixing $NiSO_4$, $NaH_2PO_2$, $Na_3C_6H_5O_7$, and $NH_4Cl$ to form a homogenous, aqueous solution. Rapamycin (sirolimus), DAA-1, and HP-1 were also added to various electroless Ni—P baths, of the same composition as the above described bath, and co-deposited therewith on the surface of the stent over the tie layer and initial Ni—P layer. The electroless Ni—P and drug co-depositions were conducted at a temperature range of 37–45 C and a pH of 9.5–10 for a total of 120 minutes. DAA-1 and HP-1 were added to their respective Ni—P baths at a concentration of 1.25 mg per 25 ml Ni—P solution. Rapamycin was added to its Ni—P bath at a concentration of 1 mg per 25 ml of Ni—P solution.

A method of applying multiple thin metallic films to thereby assemble a metallic matrix incorporating one or more biologically active agents onto an implantable device has been disclosed. Although the present invention has been described in accordance with the embodiments described, one of ordinary skill in the art will readily recognize that there could be variations to the embodiments and those variations would be within the spirit and scope of the present invention.

For example, a biodegradable polymer top coat can be applied over the metallic composite matrix to delay or control release of the therapeutic agents from the matrix.

In addition, multiple layers containing different drugs can be applied by sequential immersion in multiple electroless electrochemical baths containing the different drugs. Moreover, materials such as barium or bismuth can be co-deposited in the electroless deposition step to increase the radiopacity of the implantable device.

And while devices such as joints and leads, for example, can be coated with drugs to lessen the inflammatory response, other implantable devices, such as detachable coils for treating and sealing off aneursyms, can be coated with agents to cause coagulation or a thrombogenetic response.

With regard to specific compounds that can be co-deposited in accordance with the invention, and with particular regard to stents, it is essentially limitless and includes for example; sirolimus or rapamycin and its analogs, paclitaxel and its derivatives, growth factors, heparin, aspirin, tetracycline, dexamethasone, des-aspartate angiotensin I, tachykinins, sialokinins, apocynin, siRNA, pleitrophin, exochelins, etc.

In addition, any of the aforementioned compounds could be clad with a biodegradable coating prior to mixing in the electroless bath for time release after diffusion from the metallic composite coating.

We claim:

1. A medical device comprising:
    a substrate having an outer surface; and
    a composite coating on said outer surface including a plurality of layers which are comprised of:
        a first metal layer; and
        a second metallic composite layer comprising a metal and at least one therapeutic material wherein said therapeutic material is selected from the group consisting of rapamycin (sirolimus), rapamycin (sirolimus) analogs, paclitaxel, paclitaxel derivatives, growth factors, heparin, aspirin, tetracycline, dexamethasone, des-aspartate angiotensin I, tachykinins, sialokinins, apocynin, siRNA, pleiotrophin, exochelins, and combinations thereof.

2. The medical device according to claim 1 wherein the first metal layer is electroplated on the outer surface of the substrate.

3. The medical device according to claim 1 wherein the metal comprising said first metal layer is selected from the group of metals consisting of nickel, cobalt, copper, gold, silver, platinum, chromium, palladium, and molybdenum.

4. The medical device according to claim 1 wherein the substrate is a metal or a metal alloy.

5. The medical device according to claim 4 wherein the substrate is a metal alloy selected from the group consisting of stainless steel, cobalt-chromium, nickel-titanium, platinum-iridium, and niobium-zirconium.

6. The medical device according to claim 1 wherein the substrate is a stent.

7. The medical device according to claim 1 wherein the at least one therapeutic material in said second metallic composite layer comprising a substance which is more radiopaque relative to the substrate.

8. The medical device according to claim 1 further comprising a top layer over the second metallic composite layer.

9. The medical device according to claim 8 wherein said top layer is a metallic layer.

10. The medical device according to claim 9 wherein said top layer is a polymeric material.

* * * * *